United States Patent
Queiroz et al.

(10) Patent No.: US 12,195,425 B2
(45) Date of Patent: Jan. 14, 2025

(54) PURIFICATION OF LOWER OLEFINS

(71) Applicant: Clariant International Ltd, Muttenz (CH)

(72) Inventors: Carla Moreira Santos Queiroz, Vila Theodoro Suzano (BR); Valeria Perfeito Vicentini, Vila Theodoro Suzano (BR); Michael Severance, Louisville, KY (US); Darren Adams, The Woodlands, TX (US); Palanichamy Manikandan, Louisville, KY (US); Uwe Duerr, Germering (DE); Andreas Bachmeier, Munich (DE)

(73) Assignee: CLARIANT INTERNATIONAL LTD, Muttenz (CH)

( * ) Notice: Subject to any disclaimer, the term of this patent is extended or adjusted under 35 U.S.C. 154(b) by 0 days.

(21) Appl. No.: 17/915,158

(22) PCT Filed: Apr. 21, 2021

(86) PCT No.: PCT/EP2021/060344
§ 371 (c)(1),
(2) Date: Sep. 28, 2022

(87) PCT Pub. No.: WO2021/214122
PCT Pub. Date: Oct. 28, 2021

(65) Prior Publication Data
US 2024/0043358 A1    Feb. 8, 2024

(51) Int. Cl.
| C07C 7/13 | (2006.01) |
| B01D 53/86 | (2006.01) |
| B01J 21/04 | (2006.01) |
| B01J 21/16 | (2006.01) |
| B01J 23/80 | (2006.01) |
| B01J 37/03 | (2006.01) |
| B01J 37/18 | (2006.01) |

(52) U.S. Cl.
CPC .............. *C07C 7/13* (2013.01); *B01D 53/864* (2013.01); *B01D 53/8668* (2013.01); *B01D 53/8671* (2013.01); *B01J 21/04* (2013.01); *B01J 21/16* (2013.01); *B01J 23/80* (2013.01); *B01J 37/03* (2013.01); *B01J 37/18* (2013.01); *B01D 2255/20761* (2013.01); *B01D 2255/20792* (2013.01); *B01D 2255/40* (2013.01); *B01D 2256/24* (2013.01); *B01D 2257/104* (2013.01); *B01D 2257/108* (2013.01); *B01D 2257/502* (2013.01); *B01D 2257/7022* (2013.01)

(58) Field of Classification Search
CPC .. C07C 7/13; C07C 7/12; C07C 11/04; C07C 11/06; C07C 11/08; B01D 53/864; B01D 53/8668; B01D 53/8671; B01D 2255/20761; B01D 2255/20792; B01D 2255/40; B01D 2256/24; B01D 2257/104; B01D 2257/108; B01D 2257/502; B01D 2257/7022; B01D 2253/102; B01D 2255/1021; B01D 2255/1023; B01D 2255/104; B01D 2255/2063; B01D 2255/2065; B01D 2255/20738; B01D 2255/20753; B01D 2255/50; B01D 2257/30; B01D 2257/304; B01D 2257/504; B01D 2257/80; B01J 21/04; B01J 21/16; B01J 23/80; B01J 37/03; B01J 37/18; Y02C 20/40; Y02C 20/151; Y02C 20/50; Y02C 20/52
See application file for complete search history.

(56) References Cited

U.S. PATENT DOCUMENTS

| 6,080,905 A * | 6/2000 | Kaminsky ................ B01J 20/18 |
| | | 585/820 |
| 2011/0027156 A1* | 2/2011 | Eisinger .................. B01J 20/10 |
| | | 422/187 |
| 2016/0347690 A1* | 12/2016 | Peitz ...................... C10G 45/04 |
| 2021/0138430 A1 | 5/2021 | Kojima |

FOREIGN PATENT DOCUMENTS

| CN | 106984259 | 7/2017 |
| WO | 2012032475 | 3/2012 |

OTHER PUBLICATIONS

Specification Sheet for BASF for R3-15.*

* cited by examiner

Primary Examiner — Ali Z Fadhel

(57) ABSTRACT

Disclosed herein are a bed of materials and use of it for removing contaminants not limiting to carbon monoxide, oxygen, carbon dioxide, acetylene, hydrogen, water, carbonyl sulfide and hydrogen sulfide from lower olefins without limiting ethylene.

13 Claims, No Drawings

PURIFICATION OF LOWER OLEFINS

FIELD OF INVENTION

The embodiments disclosed herein pertain to the preparation and use of a bed of material and method for purifying lower olefins, including without limitation ethylene, which can be employed with feed stream purification using a material in a single packed bed for olefin purification.

BACKGROUND

Many products are made from polymeric materials. One example is polyethylene (PE). PE is produced in various forms, including as high density polyethylene (HDPE). The ethylene monomer units that form PE in its various forms, however, must be purified for the removal of contaminants. In fact, requirements of the polymer industry in regards to the monomer purity are trending toward greater stringency. This trend is associated with a higher demand for removal of trace contaminants from monomer streams, even at ultra trace levels, prior to polymerization. Given the high sensitivity to certain contaminants, acceptable impurity levels in some polymerization processes have reduced from ppm/ppb levels down to low ppb levels. For example, metallocene catalysts exhibit a high sensitivity, and in general a number of impurities exist having the potential, even at low and varying concentrations, to impact negatively the yield and efficient production of various products, such as polyethylene.

Particularly for the PE industry, common ethylene poisons of the metallocene catalysts type include: $CO$, $CO_2$, $O_2$, acetylene, $H_2$, $H_2O$, sulfur compounds such as carbonyl sulfide (COS), hydrogen sulfide ($H_2S$), $CH_3SH$, oxygenates and nitrogen containing compounds, and others. The presence of these elements in ppm levels tends to block the catalyst active sites and reduce the productivity and overall yield of PE manufacturing. To enhance the catalytic productivity of a PE polymerization plant, conventionally the ethylene feedstock (ethylene monomer) is purified prior to the polymerization reaction.

Conventionally, multiple beds having specific catalysts or adsorbents are used to remove individual contaminants in a sequential manner at different process conditions. This approach requires substantially higher capital and operating costs and processing time. There are advantages, however, in having the inventive materials arranged on a single bed, able to remove all the contaminants in one process condition to overcome the above limitations.

Accordingly, a bed of materials and a method of purification, which may be provided in a variety of forms and alternatives in accordance with present embodiments, reduce the number of steps needed for olefins purification. As desired, these have the potential to be used as part of a purification system that employs a single large reactor.

SUMMARY OF EMBODIMENTS

According to multiple embodiments and alternatives, it will be understood that the materials disclosed herein, and methods for their production, are suitable for the removal of a broad range of contaminants, including the types of contaminating compounds mentioned herein, down to ppb levels. This bed of materials can be regenerated periodically and reused over multiple cycles. By way of illustration and not limitation, exemplary embodiments associated with the present disclosure include a bed of material compositions comprising copper catalysts with optionally one or more promoters and a support, and porous inorganic oxide supports. In some embodiments, these materials are placed in a single bed. Thus formed, a bed of materials according to multiple embodiments and alternatives can be used for ethylene purification, among other uses. These materials may be employed to remove impurities in ethylene monomer units or other products moving as a feed in a gaseous stream, in an environment (e.g., a large reactor) operating at a temperature range between about 40° C. to 120° C., at an exemplary flow rate of the entering feed ranges between about 1,000 to about 10,000 $h^{-1}$ gas hourly space velocity (GHSV), and during use at an exemplary pressure that may range from about 1 to 1,000 pounds per square inch gauge (psig). As desired, operating conditions when a feed is passed over a bed of materials can be at a temperature between about 10-70° C., more particularly between 20-50° C., and at a pressure in a range of about 5-50 bar.

As disclosed herein, such materials (e.g., a bed of materials) according to present embodiments and alternatives are suitable for use in the removal of impurities from a feed stream. An example of such a feed is a stream of ethylene monomer, or propylene or butylene monomer as non-limiting examples, traveling through a reactor. Carbon monoxide (CO) is one such impurity. CO may be removed solely, or it may be removed simultaneously with removal of other compounds, including without limitation oxygen ($O_2$), carbon dioxide ($CO_2$), acetylene, hydrogen ($H_2$), water, carbonyl sulfide hydrogen sulfide, and oxygenates. Accordingly, materials (e.g., a bed of materials) of the present embodiments can be more efficient than conventionally multi-bed systems. Further, they reduce the time and cost needed for PE production (as one example), reduce other possible capital costs, and provide for other uses that require purification of gaseous streams.

MULTIPLE EMBODIMENTS AND ALTERNATIVES

In some embodiments, the materials (e.g., arranged as a bed of materials) of the present disclosure comprise copper catalysts with optionally one or more promoters and supports, and porous inorganic oxides. In other embodiments, the promoters are selected from Fe, Ni, Zn, La, Ce, Zr, Mg, Mn, Pd, Pt (to include compounds containing these elements) and combinations thereof. In yet other embodiments, the support is selected from activated carbon, carbon nanotube, alumina, modified alumina, silica, zeolites, zirconia, ceria. In some embodiments, a porous inorganic material comprising one or more of alumina, zeolite, clay and combinations thereof is incorporated in the materials. Embodiments according to the present disclosure include, without limitation, materials comprising zeolites selected from naturally occurring or synthetically made materials, and clay selected from sodic bentonite clay or layered double hydroxide clay.

In some embodiments, formation of materials in a bed comprises mechanical mixing of different components, followed by extrusion and drying. Optionally, the material is pelletized after drying. In some embodiments, these materials are subjected to reduction using a stream comprising of $H_2$ with optionally additional gases such as methane, $N_2$.

EXAMPLES

Example 1—Production of CuOZnO

CuOZnO composites are synthesized by coprecipitation. According to one such known method, a mixed metal nitrate solution was prepared having a concentration of 40 g/L for Cu nitrate and 80 g/L for Zn nitrate. The solution was then coprecipitated with 170 g/L of a sodium carbonate solution, keeping the pH between 6 to 8 units, and this precursor material was then aged under stirring for 2 hours until a cake was formed. The cake was then filtered in a filter press and washed until electrical conductivity measured less than 50 microsiemens. The washed cake was spray dried to generate a CuOZnO powder, then calcined at 450° C. for 4 hours in a rotary calciner.

Example 2—Production of a Bed of Material

A material was produced by mixing powder by weight of 75 g of activated alumina, g of sodic bentonite clay and 20 g of CuOZnO (catalyst, Cu/Zn weight ratio of 1 to 2). Granulometry of the powder was less than 100 mesh. Mixing was accomplished by using a kneader mixer. After complete homogenization of the starting materials was achieved by adding 150 ml of water, the material was extruded to a size of 6 mm×3 mm and dried at 85° C. for 12 h.

Examples 3-6

The following examples in Table 1 (Examples 3-6) set forth weight percentages of a group of exemplary materials, which, except for one of the examples, were formed by the process steps set forth in Example 2. However, Example 6 was formed from uncalcined CuOZnO powder, which was extruded and dried at 85° C., followed by calcination at 600° C. for one hour:

TABLE 1

|  | Example 3 | Example 4 | Example 5 | Example 6 |
|---|---|---|---|---|
| activated alumina | 58% | 50% | 75% | — |
| CuOZnO | 40% | 50% | 19.94% | 100 |
| CuFeCe | — | — | — | — |
| sodic bentonite clay | 2% | — | 5% | — |
| promoter | — | — | 0.06% (Pd or Pt) | — |

Examples 7-9

The following examples in Table 2 (Examples 7-9) set forth weight percentages of different component materials, generally made by the process steps set forth in Example 2:

TABLE 2

|  | Example 7 | Example 8 | Example 9 | Example 10 |
|---|---|---|---|---|
| activated alumina | 75% | 50% | 38% | 75% |
| CuZn adsorber | 19.9% | 5% | 20% | — |
| CuFeCe adsorber | — | — | — | 20% |
| sodic bentonite clay | 5% | 5% | 5% | 5% |
| promoter | 0.1% (NiO, Ag$_2$O or La$_2$O$_3$) | — | — | — |
| zeolite 13X | — | — | 40% | 37% |

Example 10—an Embodiment for Coprecipitation of CuFeCe

A CuOZnO$_x$ was prepared by coprecipitation in accordance with the procedure in Example 1, described for a CuOZnO, except nitrates solutions were in the concentration of 55 g/L for Cu, 300 g/L for Fe and 15 g/L for Ce. Using the CuOZnO$_x$ formed in this manner, a product was then formed in accordance with the procedures of Example 2, and containing the weight percentages set forth in Table 2, above, for Example 10.

Example 11—Use of Bed of Materials for Ethylene Purification

In these tests, the respective bed material was crushed to a size of 1.2 to 1.4 mm. In one aspect, the bed materials of Examples 1-10 were reduced in situ using 10% H$_2$ in N$_2$ at 200° C. for 12 hours, then using 99.99% H$_2$ for 2 hours before subjecting the materials for impurity removal experiments. Examples 2-10 were tested for removal of CO and simultaneous removal of oxygen, acetylene and hydrogen (referred to collectively as simultaneous contaminants removal). A fixed bed reactor was loaded with 15 mL of crushed bed materials according to the present embodiments, maintaining a D/Dp ratio (particle diameter per reactor diameter) greater than 10. As desired to further prepare the bed, prior to passing the feed over the bed, the bed material may be passed through a reducing gas stream comprising hydrogen, nitrogen, and methane at a temperature of 100-400° C., with the copper in substantially reduced form. Each of the runs was conducted at a GSHV range from 1,000 to 10,000 h$^{-1}$, varying the temperature from 40° C. to 100° C. as discussed below, and the tests were run for at least ten hours at each temperature condition. Optionally, the GSHV could be run at 1000-5000 h$^{-1}$. An ethylene gas (i.e., monomer to be converted later into polyethylene) comprised of 10 ppm of CO (one of the exemplary contaminants or impurities) fed the reactor at 25 bar (g). For experiments directed to simultaneous contaminants removal, a commercial ethylene gas mixture contaminated with 10 ppm CO, 20 ppm O$_2$, 10 ppm acetylene and 80 ppm H$_2$ was used.

With regard to Examples 2-6, at a temperature of 40° C. and GHSV of 3,000 h$^{-1}$, results of testing showed >99% removal of CO as well as simultaneous removal of >99% of contaminants after at least 30 hours on stream. At a temperature range from 80° C. to 100° C., results of testing showed >99% removal of CO as well as simultaneous removal of >99% of contaminants after at least 30 hours on stream.

With regard to Examples 7-10, at a temperature of 40° C. and GHSV of 1,000 h$^{-1}$, results of testing showed >99% removal of CO as well as simultaneous removal of >99% of contaminants after at least 30 hours on stream. At a temperature range from 80° C. to 100° C., results of testing showed >99% removal of CO as well as simultaneous removal of >99% of contaminants after at least 24 hours on stream.

As previously described, Example 1 provides a comparative example utilizing a CuOZnO synthesized by previously known coprecipitation techniques. At a temperature of 40° C. GHSV of 1,000 h$^{-1}$, results of testing showed >99% removal of CO as well as simultaneous removal of >99% of contaminants after at least 30 hours on stream. At a temperature range from ° C. to 100° C. and GHSV range from 1,000 h$^{-1}$ to 3,000 h$^{-1}$, results of testing showed >99% removal of CO as well as simultaneous removal of >99% of contaminants after at least 24 hours on stream. In addition, Example 1 resulted in CO$_2$ at levels greater than >10 ppmv (part per million by volume) when fed through the reactor at a temperature of 40° C. at a GHSV of 3,000 h$^{-1}$ wherein usually one needs to have additional beds to remove $CO_2$ and $H_2O$ if any.

Accordingly, Examples 2-10 are illustrative of a method of forming, and a group of bed materials obtained by the practice of such methods, all in accordance with present embodiments. For these examples, the bed materials were found to remove >99% of all CO from the gaseous streams. Likewise, they were found to simultaneously remove all major contaminants from a concentration in the ppm range to ppb levels (much less than 0.1 ppm).

The results in Examples 2-10 are comparable with the results from the practice of Example 1 (comparative example), but the former are associated with fewer manufacturing steps, and thus reduced time, and reduced cost compared to conventional practices such as Example 1, which also requires additional bed(s) usually with molecular sieves to remove CO and $H_2O$. While Examples 2-10 are provided, many other variations and alternatives are included within the scope of multiple embodiments and alternatives provided for and contemplated herein.

It will be understood that the embodiments described herein are not limited in their application to the details of the teachings and descriptions set forth. Rather, it will be understood that the present embodiments and alternatives, as described and claimed herein, are capable of being practiced or carried out in various ways. Also, it is to be understood that words and phrases used herein are for the purpose of description and should not be regarded as limiting. The use herein of such words and phrases as "including," "such as," "comprising," "e.g.," "containing," or "having" and variations of those words is meant to encompass the items listed thereafter, and equivalents of those, as well as additional items.

Accordingly, the foregoing descriptions of embodiments and alternatives are meant to illustrate, rather than to serve as limits on the scope of what has been disclosed herein. The descriptions herein are not meant to limit the understanding of the embodiments to the precise forms disclosed. It will be understood by those having ordinary skill in the art that modifications and variations of these embodiments are reasonably possible in light of the above teachings and descriptions.

The invention claimed is:

1. A process for the purification of impurities or contaminants of lower olefins comprising passing a feed over a single bed of material, the material comprising copper, at least one promoter, at least one support, and at least one porous inorganic oxide, wherein prior to passing the feed over the bed of material, the material is reduced with a reducing gas stream comprising hydrogen, nitrogen, and methane at a temperature of 100-400° C.

2. The process of claim 1, wherein the promoters are selected from Fe, Ni, Zn, La, Ce, Zr, Mg, Mn Pd, Pt, Ru, and Rh, and combinations thereof.

3. The process of claim 1, wherein the support is selected from activated carbon, carbon nanotube, alumina, modified alumina, silica, zeolites, zirconia, ceria.

4. The process of claim 1, wherein the porous inorganic oxide comprises at least one of alumina, zeolite, and clay, and combinations thereof.

5. The process of claim 1, wherein the contaminants comprise at least one of CO, $H_2$, C2 or C3 acetylene, $H_2O$, $CO_2$, $H_2S$, methanol, arsine, and phosphine.

6. The process of claim 1, resulting in removal of each contaminant below a level of 0.1 ppm.

7. The process of claim 1, wherein the feed is passed over the bed at a temperature between about 10-70° C., and at a pressure in a range of about 5-50 bar.

8. The process of claim 7, wherein the temperature is between 20-50° C.

9. The process of claim 1, wherein the bed is heated under a stream of inert gas comprising nitrogen and methane to a temperature of 100-400° C. for 1-24 hours.

10. The process of claim 9, wherein the copper is substantially in reduced form.

11. The process of claim 1, wherein the lower olefins are chosen from ethylene, and propylene, and butylene.

12. The process of claim 1, wherein the concentration of copper is no greater than 50 wt %.

13. The process of claim 12, wherein the concentration of copper is no greater than 20 wt %.

* * * * *